United States Patent [19]

Naglieri et al.

[11] 4,115,419

[45] Sep. 19, 1978

[54] PROCESS FOR CONVERTING THALLIUM (I) TO THALLIUM (III)

[75] Inventors: Anthony N. Naglieri, Pine Brook; Nabil Rizkalla, River Vale, both of N.J.

[73] Assignee: Halcon International, Inc., New York, N.Y.

[21] Appl. No.: 789,052

[22] Filed: Apr. 21, 1977

[51] Int. Cl.² ............................................. C01F 5/00
[52] U.S. Cl. ............................ 260/429 R; 423/395; 423/495; 423/544; 423/659
[58] Field of Search ................ 260/429 R; 423/395, 423/495, 544, 659

[56] References Cited

U.S. PATENT DOCUMENTS

| | | | |
|---|---|---|---|
| 3,399,956 | 9/1968 | Hirose et al. | 423/495 |
| 3,436,409 | 4/1969 | Hill et al. | 260/348.5 |
| 3,479,262 | 11/1969 | MacLean et al. | 204/80 |
| 3,816,540 | 6/1974 | Barone et al. | 260/610 B |

FOREIGN PATENT DOCUMENTS

| | | | |
|---|---|---|---|
| 13,104 | 2/1974 | Japan | 260/429 R UX |
| 44,116 | 11/1976 | Japan | 260/429 R UX |

OTHER PUBLICATIONS

Spencer, L. Anorg. Chem. v44, pp. 399–407 (1905).

*Primary Examiner*—Helen M. S. Sneed
*Attorney, Agent, or Firm*—William C. Long; David Dick; Jack B. Murray, Jr.

[57] ABSTRACT

A monovalent thallium compound is converted to a trivalent thallium compound by treating the thallium (I) compound with an organic hydroperoxide in the presence of a Group VIII noble metal catalyst in a liquid medium and in the presence of a promoter comprising a member selected from the group consisting of alkali metal compounds and heterocyclic tertiary amines, to oxidize the thallium (I) compound to a thallium (III) compound.

10 Claims, No Drawings

PROCESS FOR CONVERTING THALLIUM (I) TO THALLIUM (III)

This invention relates to the oxidation of thallium (I) to thallium (III).

Trivalent thallium compounds, i.e., thallic compounds, have been used as oxidizing agents in various reactions. For example, Kruse et al. *I. Org. Chem.* 36, 1154 (1971) describe the epoxidation of certain olefins with thallic acetate and U.S. Pat. No. 3,641,067 relates to the preparation of the epoxides of propylene and isobutylene by means of lower thallic alkanoates.

In all of these reactions the trivalent thallium is reduced to the monovalent state and, if the thallium is to be reused in the reaction, it is necessary to reoxidize or "regenerate" it by converting thallium (I) to thallium (III). Various methods for effecting this conversion have been proposed and are more or less effective. Thus, U.S. Pat. No. 3,399,956 (issued to Hirose et al.) describes the oxidation of Tl(I) to Tl(III) by means of molecular oxygen in an acidic aqueous medium containing chloride or bromide ions and an ion of a redox metal such as copper, mercury, chromium, manganese, iron, cobalt, and nickel. Hirose et al. refer to earlier processes for effecting the conversion of Tl(I) to Tl(III) and point out the problems involved in achieving the desired oxidation and the disadvantages and drawbacks of prior procedures. While the Hirose et al. process is described as an improvement over processes previously proposed, it is limited to the use of aqueous chloride or bromide solutions so that the thallium (III) is always produced as a chloride or bromide and it is generally necessary to use the redox metal in large amounts in relation to the thallium compound being treated.

It is an object of this invention to provide an improved process for the oxidation of monovalent thallium to trivalent thallium.

It is a further object of the invention to provide a process of the character indicated which is not limited to specific reaction media.

CROSS-REFERENCE TO RELATED APPLICATIONS

In application of W. F. Brill, entitled "Process for Converting Thallium (I) to Thallium (III)," Ser. No. 691,114, filed May 28, 1976, now abandoned, it is proposed to convert thallium (I) to thallium (III) by means of an organic hydroperoxide using a Group VIII noble metal as a catalyst. In the absence of a promoter, however, a conversion of, the thallium (I) to thallium (III) in excess of from about 70 mol % is difficult to obtain.

In our copending application entitled "Conversion of Thallium (I) to Thallium (III)," Ser. No. 740,148, filed, Nov. 8, 1976 we disclose our discovery of the use of heterocyclic tertiary amines as promoters for the conversion of thallium (I) to thallium (III) using molecular oxygen in the presence of a Group VIII noble metal catalyst.

Application of R. Johnson entitled "Conversion of Mono-Valent Thallium to Tri-Valent Thallium," Ser. No. 740,147, filed Nov. 8, 1976, relates to a process for converting Thallium (I) to Thallium (III) by using molecular oxygen in the presence of a Group VIII noble metal catalyst and in the presence of an alkali metal compound as promoter.

In accordance with the invention, a monovalent thallium compound is converted to a trivalent thallium compound by treating the thallium (I) compound with an organic hydroperoxide in the presence of a Group VIII noble metal catalyst and in the presence of a promoter comprising a member selected from the group consisting of heterocyclic tertiary amines and alkali metal compounds, to oxidize the thallium (I) compound to achieve high conversions to thallium (III) in a rapid and efficient manner.

The Group VIII Noble metals comprise platinum, palladium, rhodium, ruthenium, osmium annd iridium, but platinum, palladium, ruthenium and rhodium are preferred, especially platinum and palladium. Mixed catalysts can be used if desired. The catalyst is preferably used in a heterogenous system, e.g., in the form of a fixed bed over which the reaction medium is passed or in the form of a suspension. In the former case the catalyst is ordinarily supported upon a solid carrier, but it is also possible to use the catalyst in a homogenous system, i.e., it may be employed in a form which is soluble in the reaction medium. Thus, the Group VIII noble metal catalyst may be suitably added as a compound of the above-mentioned metals, e.g., an oxide, preferably on a carrier, but it is most preferred to add the catalyst as the fine-divided metal, e.g., platinum black, or as the metal supported on a carrier.

In the case of a homogeneous system, the metal is eventually converted to a compound sufficiently soluble to provide a catalytic amount of the metal in solution in the reaction mixture. The nature of the compound of the Group VIII noble metal is not critical and any convenient compound may be used. For example, typical compounds include the oxides, the inorganic salts such as the salts of mineral acids, e.g., the chlorides and oxychlorides, the iodides, the fluorides, the phosphates, the sulfates and the sulfites, the sulfides, and the hydroxides. Other typical compounds include salts of organic acids such as acetates or other carboxylates, organo-metallic compounds such as tetramethyl platinum, carbonyls and carbonyl halides. Also various chelates, association compounds and enol salts may be used. Further illustrative of such compounds are palladium acetate, rhodium chloride, platinum oxide (Adams catalyst), chloroplatinic acid, platinum tetrachloride, platinum diamino dinitrite, platinum cyanide, sodium tetrachloroplatinite, potassium tetrachio platinate, platinum dicarbonyl dichloride, platinum acetyl acetonacetate, tetrakis (triphenyl phosphine) platinum, tetramine platinum chloride, and corresponding compounds of the other Group VIII noble metals.

When the Group VIII noble metal catalyst is supported upon a carrier, the carrier or substrate which is employed is suitably in the form of a porous solid of such size that it can be readily dispersed in the liquid reaction medium, e.g., from 400 mesh/inch to ½ inch particle sizes. Such carrier materials are exemplified by pumice, alumina, silica, silica-alumina, magnesia, diatomaceous earth, bauxite, titania, zirconia, clays, both natural and acid treated such as Super-Filtrols, attapulgus (attapulgite), lime, magnesium silicate, silicon carbide, activated and unactivated carbons, zeolites as well as the zeolitic molecular sieves, solid foams, such as ceramic honeycombs, and porous organic polymers. The above carriers are suitably used in the form of regular and irregular particles such as tubes, balls, broken pieces, and the like. Such supported forms of the Group VIII noble metals and their compounds are prepared by conventional methods, e.g., deposition from a solution, for example as described in U.S. Pat. No.

3,717,670 in connection with rhodium compounds and, indeed, many such supported catalysts are available commercially, particularly in the case of the zero valent free metal which is an effective form for use in this invention.

Concentrations of the Group VIII noble metal component on the support can vary widely but illustrative concentrations lie within the range of 0.1 to 20 wt. %. Higher concentrations may, however, be used if desired.

The ratio of catalyst to monovalent thallium compound can also vary over a wide range. For example, 0.1 to 40 mols of catalyst per 100 mols of monovalent thallium compound are advantageously used, but lesser or greater amounts may be employed, if desired, the upper limit being determined only by economic considerations and the lower limit only by the amount which will be catalytically effective. In any case, only catalytic quantities are required to bring about a rapid conversion.

The reaction of this invention is carried out broadly using an organic hydroperoxide reactant having the formula ROOH wherein R is an organic radical. In preferred practice R is a substituted or unsubstituted alkyl, cycloalkyl, aralkyl, aralkenyl, hydroxyaralkyl, cycloalkenyl, hydroxycycloalkyl, and the like radical having about 3 to 20 carbon atoms. R may be a heterocyclic radical, preferably 4 to 10 and most preferably 5 to 8 carbon atoms. Illustrative hydroperoxides are cumene hydroperoxide, ethylbenzene hydroperoxide, tertiary butyl hydroperoxide, tetralin hydroperoxide, methylcyclohexene hydroperoxide, and the like as well as the hydroperoxides of toluene, p-ethyl toluene, isobutylbenzene, diisopropyl benzene, p-isopropyl toluene, o-xylene, m-xylene, p-xylene, phenyl cyclohexane, etc. Particularly preferred are tertiary butyl hydroperoxide and ethylbenzene hydroperoxide. Hydroperoxides are well-known compounds which are readily produced in known manner by the oxidation of the corresponding hydrocarbon as described, for example, in U.S. Pat. No. 3,816,540 to which reference is made for examples of other hydroperoxides which are suitably used in the process of this invention.

The ratio of organic hydroperoxide to thallium compound can vary over a wide range but suitably at least 0.1 mol of hydroperoxide per mol of thallous compound is used. There is no particular advantage in using more than one mol of hydroperoxide per mol of thallium compound but greater quantities can, of course, be used, e.g., up to 10 mols per mol. All of the hydroperoxide can be initially charged or it can be added in portions as the reaction proceeds, e.g., incrementally.

An advantage of the use of an organic hydroperoxide in accordance with this invention is the fact that during the oxidation reaction the organic hydroperoxide, ROOH, is converted to the corresponding alcohol, ROH. This alcohol can itself be recovered as a valuable coproduct of the process or reconverted to the hydroperoxide by procedures such as dehydration to olefin, hydrogenation of the olefin, and oxidation to hydroperoxide, or by hydrogenolysis to hydrocarbon followed by oxidation to hydroperoxide. Thus, the oxidizing agent is, during the oxidation, converted to a product suitable for convenient regeneration of the hydroperoxide for further use.

The promoters which may be employed in the practice of this invention comprise members selected from the group consisting of heterocyclic tertiary amines, alkali metal compounds and mixtures thereof. The heterocyclic tertiary amines which can be employed may contain one or more nitrogen atoms and one or more rings. Examples of amines of the character indicated which are normally liquid at room temperatures include pyridine, the alkyl-substituted pyridines, such as the picolines, the lutidines and the like, quinoline, lepidine, quinaldine and other alkyl-substituted quinolines, isoquinoline and alkyl-substituted iso-quinolines, pyrimidine, pyridazine, alkyl N-substituted heterocyclic secondary amines such as N-methyl imidazole, N-methyl piperidine, the N-methyl pipecolines, N-methyl pyrrolidine, N-methyltriazole, and the like. The alkyl substituents preferably are lower alkyl, i.e., 1 to 5 carbon atoms. Higher-melting heterocyclic amines and heterocyclic tertiary amines which are substituted by groups other than alkyl such as hydroxy, halo, alkoxy, and like groups which are non-reactive in the system are also suitably used. Examples of such promoters are hydroxy pyridines, e.g., 2-hydroxypyridine, e.g., 2,2-bipyridine, chloropyridines such as 2-chloropyridine and like halo-substituted pyridines and quinolines, 4-methoxypyridine and like alkoxy pyridines and quinolines, 2-phenyl pyridine and like phenylsubstituted pyridines and quinolines, pyrazine, phenanthridine, phthalazine, quinazoline, quinoxaline, cinnoline, isoxazole, N-methyl indole, and the like. It is to be understood, however, that the foregoing named heterocyclic amines are given for illustrative purposes only. The amount of such amine promoter should ordinarily be at least 0.1 mol per mol of thallium (I) compound being treated, preferably at least 1 mol per mol. The upper limit is not critical and may, for example, be 500 mols of amine promoter per mol of thallium (I) compound or more. The upper limit is determined only by practical economic considerations.

Also suitable as promoters for the Group VIII noble metal catalyst in accordance with the invention are alkali metal compounds, i.e., compounds of a metal of Group IA of the Periodic Chart of the Elements. Preferred are compounds of sodium, potassium, rubidium and cesium. The compound is generally one that is soluble in the reaction mixture. Typical compounds are the oxides, hydroxides, salts, both organic and inorganic, such as the carboxylates, the carbonates, and the like. Preferably the compounds give a basic reaction. Most preferably the carboxylates are used and these may be alkyl carboxylates, including cycloalkyl carboxylates, or aryl carboxylates, e.g., acetates, propionates, butyrates, benzoates, and the like, preferably containing up to 20 carbon atoms in the organic moiety. Most preferably, the alkali metal compound has an anion corresponding to the anion of the thallium (I) being treated. The amount of alkali metal promoter is not critical and ordinarily can vary from 0.01 to 50 moles per mole of thallium (I) compound, preferably 0.1 to 10 moles.

Ordinarily, the higher the reaction temperature, the greater the reaction rate. It is unnecessary, however, to employ high temperatures. Normally, the reaction temperature may range from 10° to about 150° C. Typically, temperatures of 20° to 100° C. are used, but higher or lower temperatures are operable. Excessively high temperatures, however, are not advantageous because they may eventually result in reaction between the thallium compounds and the solvent.

Total pressure is not a specific parameter of the process and subatmospheric, atmospheric or superatmospheric pressures may be employed. Ordinarily, atmospheric pressure is entirely suitable. It is generally desirable to stir the reaction medium, particularly when a dispersed heterogenous catalyst is employed, and this may be effected by mechanical agitation, shaking, and like means known to the art.

Any convenient monovalent thallium compound can be treated in accordance with the invention. Typically, the compound will be a salt which may be organic, such as carboxylate of an alkyl, cycloalkyl or aryl carboxylic acid containing up to 20 carbon atoms, such as an acetate or benzoate, or inorganic, such as a nitrate, a sulfate, or a halide, but other compounds may be used, such as hydroxides, if desired. The thallous compound is suitably one which is at least partly soluble in the liquid employed.

The thallous compounds resulting from the epoxidation reactions described in the above-mentioned Kruse et al. article and U.S. Pat. No. 3,641,067 will be carboxylates and it is a feature of this invention that such thallous carboxylates can be converted to the thallic carboxylates with ease so that the conversion products can be recycled to the epoxidation reaction.

The reaction medium for the conversion of monovalent thallium to trivalent thallium can be aqueous or non-aqueous. Non-aqueous media comprise organic solvents of various types as are well known to the art, including polar and non-polar solvents, but the polar solvents are particularly preferred. Typical polar organic solvents include the carboxylic acids such as acetic acid, ethers such as tetrahydrofuran and p-dioxane, dimethyl ethers of diethylene glycol and of triethylene glycol, alcohols such as t-butyl alcohol and methanol, ether alcohols such as polyglycols, nitriles such as acetonitrile and propionitrile, amides such as dimethyl formamide and dimethyl acetamide, ketones such as acetone, methyl ethyl ketone and diethylketone, polar chlorinated hydrocarbons such as chloroform, as well as dimethyl sulfoxide, and the like, glycol ethers such as diethylene glycol, ethylene glycol, ethylene glycol dimethyl ether, ethylene glycol diethyl ether, and diethylene glycol diethyl ether, glycol esters such as ethylene glycol diacetate, diethylene glycol diacetate, and the corresponding ethers and esters of propylene glycol, butylene glycol, and the like. The normally liquid heterocyclic tertiary amines which may be used as promoters in accordance with the invention, such as those previously named, can serve as solvents by themselves and no additional solvent is necessary but preferably they are used in combination with a solvent of the type mentioned above. Non-polar solvents include the hydrocarbons and chlorinated hydrocarbons such as carbon tetrachloride. It will be understood that a solvent is preferably chosen which is not susceptible to oxidation under the particular conditions selected for the oxidation.

While water can be used as the sole reaction medium, or an organic solvent can be used as the sole solvent component, in addition to a heterocyclic amine promoter (where employed), a water-polar organic solvent mixture containing up to about 90 volume percent water, typically 5-50% water, can also be used. When water is present, and acids are absent, the trivalent thallium produced will normally be converted into the hydroxide which will precipitate and can be readily recovered and converted into any desired thallic salt in conventional manner, e.g., the hydroxide can be converted to a thallic salt by reaction with the appropriate acid. In a preferred embodiment, a carboxylic acid providing an anion to combine with all of the thallium (III) formed is present.

If an anion corresponding to the anion of the thallous compound is present, then the thallic compound will be obtained in the form of a salt containing that anion. On the other hand, other thallium salts can be formed by supplying the appropriate anion, e.g., by adding to the reaction mixture a mineral acid such as nitric acid, or a carboxylic acid such as benzoic acid providing an anion different from the anion of the thallium salt charged. For example, if the monovalent thallium is in the form of an acetate, then acetic acid is advantageously included in the reaction mixture so that all of the trivalent thallium will also be obtained in the form of the acetate. Sufficient acetic acid is, of course, present to provide the necessary molecular quantity. Similarly, if a benzoate or propionate is desired, then benzoic acid or propionic acid, respectively, is added to the reaction medium. As previously indicated, the carboxylic acid can also serve as a solvent. The thallium (III) compound can thus be obtained in various forms as desired and as mentioned, it can be in the same form as the thallium (I) compound supplied. The acids added to provide the anion for the thallium (III) compound can be any of the acids mentioned above in connection with the thallium (I) salt subjected to treatment, e.g., carboxylic acids such as alkyl, including cycloalkyl, and aryl carboxylic acids containing up to 20 carbon atoms and which, like the anions of the thallium (I) salts, can be substituted with non-reactive substituents such as halogen, alkoxy alkyl, and the like, or mineral acids, and the like.

Thus, monovalent thallium compounds can be readily converted to trivalent thallium compounds, and the reaction medium containing the trivalent thallium compound produced can be used directly or after suitable treatment, such as filtratration to remove the solid noble metal catalyst, for epoxidation, or other reaction. The trivalent thallium compound can also be separated from the reaction medium by precipitation, evaporation of solvent, or the like, if desired.

The invention will be more fully understood by reference to the following examples of specific embodiments thereof, but it will be understood that these examples are given for illustrative purposes only and are not intended as limitative of the invention. In the Examples, determinations of thallium (III) product were carried out by means of conventional complexiometric analyses using standard ethylene nitrilo tetraacetic acid. The reaction mixture is analyzed in each case at the end of the indicated reaction period after cooling and depressurizing of the reaction vessel. Before analysis, the reaction mixture is filtered to separate the catalyst, and the filtered solids are washed with 1M acetic acid. The combined filtrate and wash solution are then subjected to analysis.

EXAMPLE 1

A 200 cc stirred autoclave is charged with a solution comprising 5 volume percent water, 80 volume percent acetic acid, 5 volume percent pyridine and 10 volume percent of a tertiary butyl alcohol solution containing tertiary butyl hydroperoxide in an amount sufficient to provide a 0.5M concentration of the hydroperoxide in the reaction mixture. The reaction mixture also contains dissolved therein a 0.25M concentration of thallous acetate, along with 10 weight percent of the reaction mixture of platinum supported on alumina in powdered form, the support containing 10% of the catalytic metal.

The autoclave is sealed and agitated at 40° C. in a constant temperature bath for a period of 1 hour. The reaction mixture is then filtered to remove catalyst, the filtered solids washed with acetic acid solution and the combined filtrate analyzed. The conversion to the thallium (III) compound is found to be 96%.

EXAMPLE 2

Example 1 is repeated except that the reaction temperature is increased to 60° C. and the reaction time is decreased to ½ hour. A 75% conversion is obtained.

EXAMPLE 3

Example 1 is repeated except that the acetic acid is replaced by an equal weight of isobutyric acid. A 97% conversion is obtained.

EXAMPLE 4

Example 1 is repeated except that an equal weight of N-methylimidazole is used instead of pyridine. Conversion of 92% is obtained.

EXAMPLE 5

Example 1 is repeated except that the pyridine is replaced by an equal weight of 2,2-bipyridine. A 94% conversion is obtained.

EXAMPLE 6

To a 200 cc stirred autoclave is charged a solution containing 20 volume percent pyridine, 10 volume percent water, 60 volume percent acetic acid and 10 volume percent of a tertiary butyl alcohol solution containing tertiary butyl hydroperoxide in an amount sufficient to provide a 0.5M concentration of the hydroperoxide in the reaction mixture. The mixture also contains 0.25M thallous acetate and 10% by weight of platinum supported on alumina in powdered form, the support containing 10% by weight of the catalytic metal. The vessel is sealed and agitated at 40° C. in a constant temperature bath for 1 hour. The reaction mixture is then filtered to remove catalyst, the filtered solids washed with aqueous acetic acid and the combined filtrate analyzed. The conversion to the thallium (III) compound is found to be 97%.

EXAMPLE 7

Example 6 is repeated except that the acetic acid is replaced with an equal weight of propionic acid. A 96% conversion is obtained.

EXAMPLE 8

Example 6 is repeated except that an equal weight of 2-hydroxypyridine is substituted for pyridine. A conversion to the thallium (III) of 95% is realized.

EXAMPLE 9

Example 6 is repeated except that an equal weight of 3-picoline is substituted for pyridine and an equal weight of propionic acid is substituted for acetic acid. A 93% conversion of thallium (I) to thallium (III) is obtained.

EXAMPLE 10

To a 200cc autoclave is charged a solution containing 20 volume percent pyridine, 10 volume percent water, 60 volume percent acetic acid and 10 volume percent of a tertiary butyl alcohol solution containing tertiary butyl hydroperoxide in an amount sufficient to provide a 0.4M concentration of the hydroperoxide in the reaction mixture. The solution charged to the reactor also contains 0.4M thallous acetate, 0.4M thallic acetate and 10 weight percent of platinum supported on alumina catalyst in powdered form, the support containing 10% of the catalytic metal. The autoclave is sealed and agitated at 60° C. in a constant temperature bath for one-half hour. After filtering of the reaction mixture, and washing of the filtered solids with aqueous acetic acid, the combined filtrate is analyzed and the conversion of the thallium (I) compounds to the thallium (III) compound is found to be 90%.

EXAMPLE 11

Example 10 is repeated except that an equal weight of a platinum supported on activated carbon, the support containing 5 weight percent of the catalytic metal, is substituted for the platinum on alumina catalyst. A 92% conversion is obtained.

EXAMPLE 12

A 200 cc stirred autoclave is charged with a solution containing 70 weight percent water, 20 weight percent acetic acid, 5 weight percent sodium acetate and 5 weight percent of a tertiary butyl alcohol solution containing tertiary butyl hydroperoxide in an amount sufficient to provide 0.5M concentration of the hydroperoxide in the reaction mixture. The reaction mixture also contains 0.25M thallous acetate. Following the procedure of Example 1, the mixture is agitated at 40° C. for a period of 1 hour, and a 96% conversion to the thallium (III) compound is obtained.

EXAMPLE 13

Example 12 is repeated except that an equal weight of cesium acetate is used instead of sodium acetate. The conversion of thallium (I) to thallium (III) is found to be 94%.

EXAMPLE 14

Example 12 is again repeated except that an equal weight of potassium acetate is used instead of sodium acetate. Analysis shows a 91% of conversion of thallium (I) to thallium (III).

EXAMPLE 15

Example 12 is again repeated except that an equal weight of lithium acetate is used instead of sodium acetate. A 92% conversion of thallium (I) to thallium (III) is obtained.

EXAMPLE 16 FOR COMPARISON

Example 1 is repeated but the pyridine is omitted from the charge, in other words, the reaction is conducted without the presence of a promoter is accordance of this invention. Analysis shows a 55% conversion of thallium (I) to thallium (III).

EXAMPLE 17

Example 1 is repeated except that an equal weight of cumene hydroperoxide is used instead of the tertiary butyl hydroperoxide. An 87% conversion of thallium (I) to thallium (III) is obtained.

EXAMPLE 18

Example 12 is repeated except that an equal weight of potassium hydroxide is used instead of the sodium acetate as promoter. Conversion of thallium (I) to thallium (III) is found to be 93%.

While the invention has been discussed above in specific connection with organic hydroperoxides of the formula ROOH, it will be understood that this formula also applies to peracids wherein R is an acyl or benzoyl group, e.g., peracetic acid, perbenzoic acid, and the like, and the term "hydroperoxide" as used herein is thus intended to cover such peracids as well.

In the foregoing examples the catalysts are commercially available products supplied by Chemical Division of Engelhard Industries and/or the Alpha Products Division of the Ventron Corporation.

Since changes may be made in carrying out the above process without departing from the scope of the invention, it is intended that all matter contained in the above description shall be interpreted as illustrative and not in a limiting sense.

What is claimed is:

1. In a process for converting a thallium (I) compound to a thallium (III) compound in which the thallium (I) compound is reacted with an organic hydroperoxide in the presence of a Group VIII noble metal, the improvement which comprises effecting said reaction in the presence of a promotor comprising a member selected from the group consisting of heterocyclic tertiary amines, and compounds of metals of Group IA of the Period Table.

2. A process as defined in claim 1 wherein the organic hydroperoxide is selected from a group consisting of compounds of the formula ROOH, wherein R is an organic radical.

3. A process as defined in claim 2, wherein the organic hydroperoxide is a peracid.

4. A process as defined in claim 1 wherein the promoter comprises a pyridine.

5. A process as defined in claim 1 wherein the reaction is carried out in a liquid medium.

6. A process as defined in claim 1 wherein the Group VIII noble metal is platinum or palladium.

7. A process as defined in claim 1 wherein the promoter is a member selected from the group consisting of sodium, potassium, cesium and rubidium.

8. A process as defined in claim 7 wherein the reaction is carried out in a liquid medium.

9. A process as defined in claim 7 wherein the Group VIII noble metal is platinum or palladium.

10. A process as defined in claim 1, wherein the thallium (I) compound is a carboxylate of an alkyl, cycloalkyl or aryl carboxylic acid containing up to 20 carbon atoms.

* * * * *